(12) United States Patent
Blain et al.

(10) Patent No.: US 11,631,341 B2
(45) Date of Patent: Apr. 18, 2023

(54) IMPACTOR MECHANISM FOR VIRTUAL REALITY SURGERY SIMULATION SYSTEM AND TELESURGERY

(71) Applicant: OSSIMTECH INC., Montreal (CA)

(72) Inventors: Andre Blain, Montreal (CA); Sebastien Delorme, Montreal (CA); Vincent Masse, Montreal (CA); Erwan Jouault, Montreal (CA); Sebastien Jomphe, Montreal (CA); Alexander Hay, Montreal (CA)

(73) Assignee: Cedarome Canada Inc. (via Symgery, a division of Cedarome Canada Inc.)

( * ) Notice: Subject to any disclaimer, the term of this patent is extended or adjusted under 35 U.S.C. 154(b) by 372 days.

(21) Appl. No.: 16/765,732

(22) PCT Filed: Nov. 16, 2018

(86) PCT No.: PCT/CA2018/051458
§ 371 (c)(1),
(2) Date: May 20, 2020

(87) PCT Pub. No.: WO2019/100148
PCT Pub. Date: May 31, 2019

(65) Prior Publication Data
US 2020/0294423 A1 Sep. 17, 2020

Related U.S. Application Data

(60) Provisional application No. 62/589,286, filed on Nov. 21, 2017.

(51) Int. Cl.
*G05B 19/19* (2006.01)
*G09B 19/24* (2006.01)
(Continued)

(52) U.S. Cl.
CPC .............. *G09B 19/24* (2013.01); *A61B 34/35* (2016.02); *A61B 90/37* (2016.02); *A61F 2/4609* (2013.01);
(Continued)

(58) Field of Classification Search
CPC ... G09B 19/24; A61B 34/35; A61B 2034/742; A61B 2090/064; A61B 2090/066; G05B 13/04
See application file for complete search history.

(56) References Cited

U.S. PATENT DOCUMENTS

| 7,001,393 B2 | 2/2006 | Schwenke et al. |
| 8,236,005 B2 | 8/2012 | Meneghini et al. |
| 2015/0282856 A1 | 10/2015 | Haiat et al. |

FOREIGN PATENT DOCUMENTS

| CA | 2823207 A1 | 7/2012 |
| CA | 2872180 A1 | 11/2013 |

(Continued)

*Primary Examiner* — Karen Masih
(74) *Attorney, Agent, or Firm* — Norton Rose Fulbright Canada LLP (57) ABSTRACT

An impactor mechanism for virtual or telepresence surgery comprises a base. An impactor shaft has a first end and a second end, a handle portion being provided at the second end. A rotational joint(s) is between the first end of the impactor shaft and the base, the joint providing two or more rotational degrees of freedom to the impactor shaft. Sensors are in the impactor mechanism for measuring an orientation of the impactor shaft relative to the base, and for measuring at least an impact force on the impactor shaft, for use in virtual surgery.

20 Claims, 6 Drawing Sheets

(51) Int. Cl.
*A61B 34/35* (2016.01)
*A61B 90/00* (2016.01)
*A61F 2/46* (2006.01)
*G09B 9/00* (2006.01)
*A61B 34/00* (2016.01)
*A61B 17/92* (2006.01)

(52) U.S. Cl.
CPC ................ *G09B 9/00* (2013.01); *A61B 17/92* (2013.01); *A61B 2034/742* (2016.02); *A61B 2090/064* (2016.02); *A61B 2090/066* (2016.02); *A61F 2002/4681* (2013.01)

(56) References Cited

FOREIGN PATENT DOCUMENTS

| CA | 2872182 | A1 |   | 11/2013 |
|----|---------|----|---|---------|
| CN | 102208150 | B | * | 3/2013 |
| CN | 105291138 | B | * | 10/2017 |
| EP | 2476397 | A1 |   | 7/2012 |
| EP | 2923677 | A1 |   | 9/2015 |
| EP | 3111897 | A1 |   | 1/2017 |
| FR | 3019031 | A1 |   | 10/2015 |

* cited by examiner

IMPACTOR MECHANISM FOR VIRTUAL REALITY SURGERY SIMULATION SYSTEM AND TELESURGERY

TECHNICAL FIELD

The present disclosure relates to virtual reality (VR) surgery simulation and telesurgery with force feedback capability.

BACKGROUND OF THE ART

Virtual reality (VR) surgery simulation is commonly used for the training of medical personnel, whether it be as part of an educational program for medical students and trainees, residents, and surgeons. VR surgery simulation is also used for surgeons to hone their skills. In VR surgery simulation, a user is provided with a graphic display of an anatomical location at which given surgical procedures must be simulated, with virtual tools being displayed as well. The user then manipulates master simulation tools to perform the surgical procedure, the position and orientation of the master simulation tools being tracked for the graphic display of virtual tools relative to the anatomical location to be updated in real-time as a function of the manipulations of the master simulation tools.

To add to the realism of VR surgery simulation, VR surgery simulation systems may have force feedback capability, also known as haptics. Force feedback is in the form of forces, vibrations, motions, produced by robotic components on the master simulation tools to emulate VR interactions between the anatomical location and the virtual slave tools. For the force feedback rendering to be accurate, robotic components, often in the form of a serial manipulator or a parallel manipulator, are provided with motors and a transmission to actuate the joints of the serial manipulator. Accuracy may often entail smaller components to provide a high bandwidth force feedback. However, some surgical procedures may require the input of excessive forces on the master simulation tools to be in conformity with real surgery. For example, in the case of hip surgery, finer movements leading to acetabulum reaming are followed up by the repeated high-force hammering of acetabular cup impaction. Hence, serial manipulators may not be adapted to reconcile finer movements with high-force manipulations.

SUMMARY

It is an aim of the present disclosure to provide a novel impactor mechanism for virtual surgery systems.

It is an aim of the present disclosure to provide a novel impactor mechanism for telesurgery.

In accordance with a first embodiment, there is provided an impactor mechanism for virtual or telepresence surgery comprising: a base; an impactor shaft having a first end and a second end, a handle portion being provided at the second end; at least one rotational joint between the first end of the impactor shaft and the base, the joint providing at least two rotational degrees of freedom to the impactor shaft; and sensors in the impactor mechanism for measuring an orientation of the impactor shaft relative to the base, and for measuring at least an impact force on the impactor shaft, for use in virtual surgery.

Further in accordance with the first embodiment, for instance, the at least one rotational joint is a spherical joint.

Still further in accordance with the first embodiment, for instance, the spherical joint is a rod end bearing, with a rod of the rod end bearing connected to the base.

Still further in accordance with the first embodiment, for instance, the rod of the rod end bearing is fixed to the base.

Still further in accordance with the first embodiment, for instance, the rod is generally horizontal.

Still further in accordance with the first embodiment, for instance, the rod end bearing has a threaded shaft portion, the impactor shaft being threadingly engaged to the threaded shaft portion.

Still further in accordance with the first embodiment, for instance, a releasable connection is between the impactor shaft and the at least one rotational joint.

Still further in accordance with the first embodiment, for instance, the base has a block connected to the at least one joint, a casing receiving the block, and at least one translational joint between the block and the casing providing at least one translational degree of freedom.

Still further in accordance with the first embodiment, for instance, two of the translational joint are provided, the block displaceable in a horizontal plane.

Still further in accordance with the first embodiment, for instance, at least one shock absorption device is provided for opposing a force against movement in each said translation degree of freedom.

Still further in accordance with the first embodiment, for instance, the at least one shock absorption device is at least one coil spring.

Still further in accordance with the first embodiment, for instance, a translational joint may be at the second end of the impactor shaft, the translational joint being connected to an impactor head at the second end.

Still further in accordance with the first embodiment, for instance, the shaft has a tubular portion, the translational joint being received in a cavity of the tubular portion.

Still further in accordance with the first embodiment, for instance, one of the sensors is at least one force sensor in the cavity.

Still further in accordance with the first embodiment, for instance, a direction of the translational joint is parallel to a longitudinal axis of the impactor shaft.

Still further in accordance with the first embodiment, for instance, the translational joint includes at least one hollow-lock set screw received in the cavity of the tubular portion, the translational joint having a rod slidingly engaged in the at least one hollow-lock set screw.

Still further in accordance with the first embodiment, for instance, the rod has at least one sleeve interfaced with the at least one hollow-lock set screw, the sleeve being on a threaded rod portion of the rod.

Still further in accordance with the first embodiment, for instance, the at least one hollow-lock set screw has a hexagonal central bore for sliding engagement of the rod therein.

Still further in accordance with the first embodiment, for instance, axes of the at least two rotational degrees of freedom intersect each other.

Still further in accordance with the first embodiment, for instance, the sensors include at least one accelerometer on the impactor shaft.

Still further in accordance with the first embodiment, for instance, the at least one accelerometer is closer to the first end of the impactor shaft than to the second end of the impactor shaft.

Still further in accordance with the first embodiment, for instance, the sensors include at least one torque sensor.

In accordance with a second embodiment, there is provided a virtual surgery system comprising: an impactor mechanism as described above or herein; a virtual surgery processor unit for receiving the orientation of the impactor shaft and the impact force, and configured for driving an implant in a bone as a function of the orientation and the impact force at a slave end; and a display unit for displaying the driving of the implant in the bone at the slave end.

Further in accordance with the second embodiment, for instance, the display unit includes a virtual reality headset.

Still further in accordance with the second embodiment, for instance, the display unit includes at least one screen.

Still further in accordance with the second embodiment, for instance, the at least one screen is horizontal.

Still further in accordance with the second embodiment, for instance, the virtual surgery processor unit provides an augmented reality output in the display unit.

Still further in accordance with the second embodiment, for instance, a haptic mechanism may be separated from the impactor mechanism, the haptic mechanism operated by the virtual surgery processor unit.

Still further in accordance with the second embodiment, for instance, the haptic mechanism is releasably connectable to the impactor mechanism to provide force feedback to the impactor mechanism.

Still further in accordance with the second embodiment, for instance, the slave end includes a telesurgery system.

Still further in accordance with the second embodiment, for instance, the slave end is a virtual reality surgery simulation session.

In accordance with a third embodiment, there is provided a virtual surgery system comprising: an impactor mechanism as described above or herein; a virtual surgery processor unit for receiving the orientation of the impactor shaft and the impact force, and configured for removing osteoma or osteophyte as a function of the orientation and the impact force at a slave end; and a display unit for displaying the removal of osteoma or osteophyte at the slave end.

DETAILED DESCRIPTION

Figure 1:
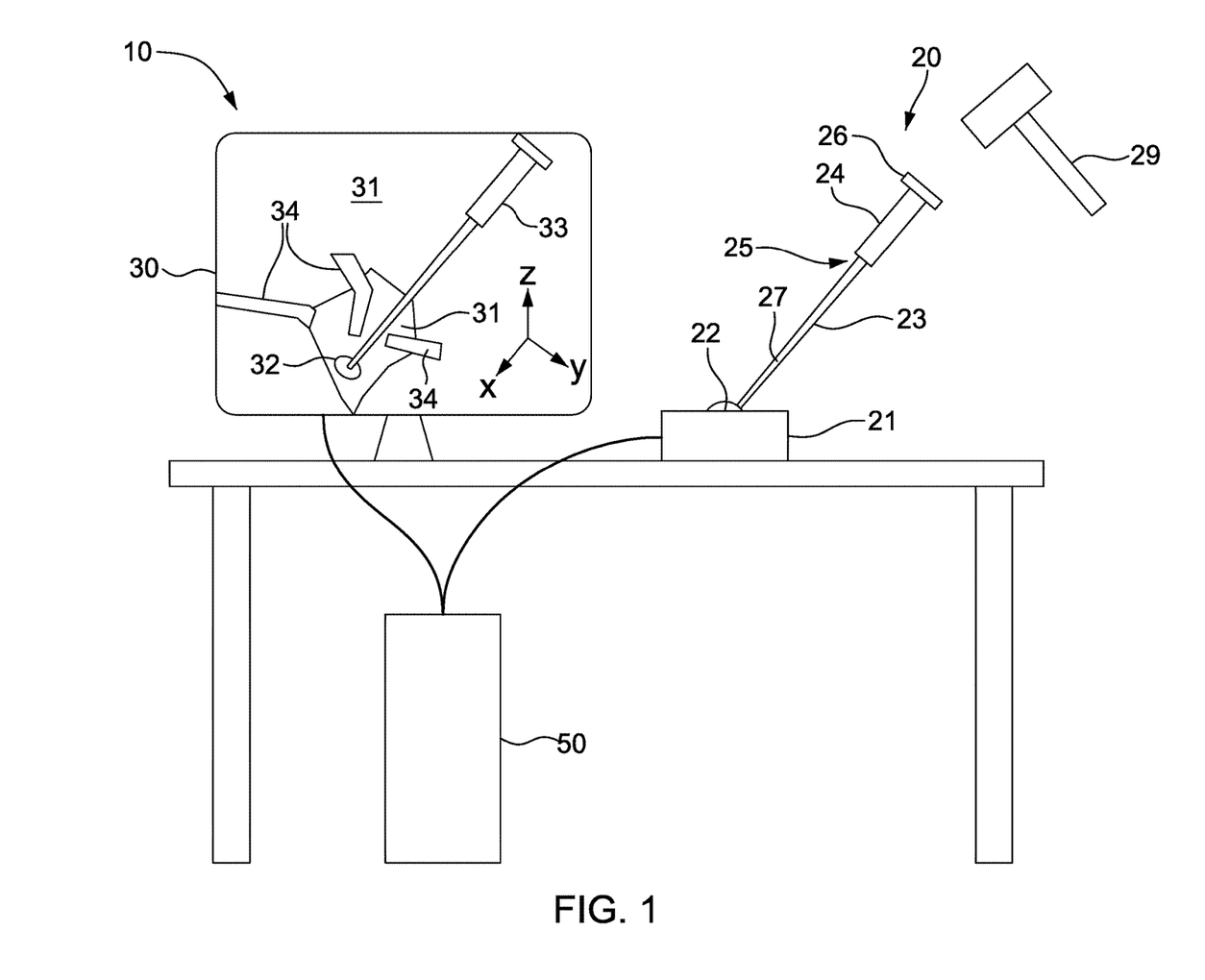
FIG. 1 is a schematic view of a virtual surgery system with an impactor mechanism in accordance with the present disclosure.
Figure 2:
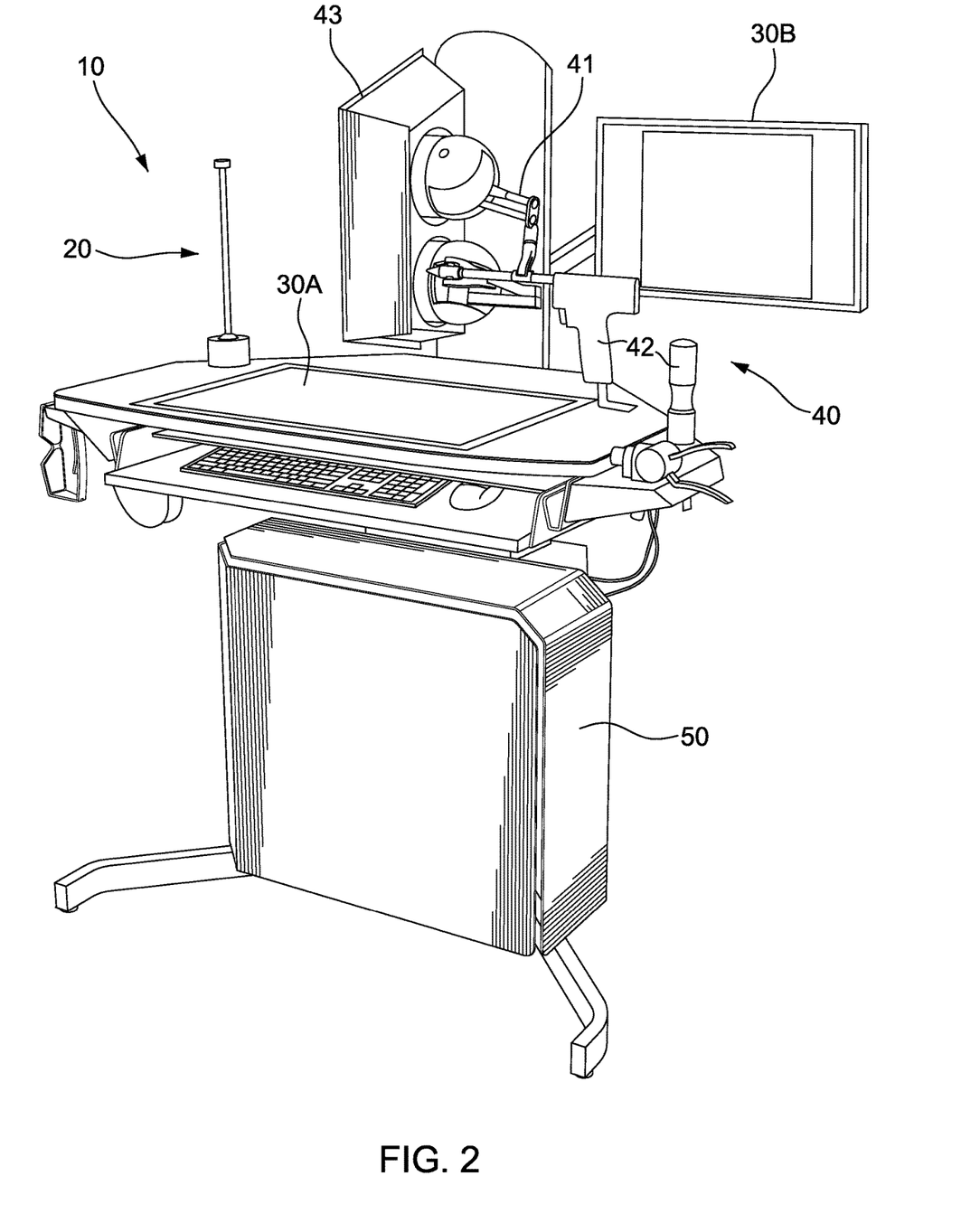
FIG. 2 is a perspective view of another embodiment of the virtual surgery system with an impactor mechanism in accordance with the present disclosure.

Referring to FIGS. 1 and 2, there is shown a virtual surgery system at 10 with an impactor mechanism 20. The virtual surgery system 10 may be a virtual reality (VR) surgery simulation system, in which a VR surgery simulation session is performed. Accordingly, the system 10 may have an impactor mechanism 20, a display unit 30, a haptic system 40, and a virtual surgery processor unit 50:

The impactor mechanism 20 is the master device (master impactor) manipulated by a user of the system 10 to control the slave impactor device in the simulation session, or in a telesurgery session (also a form a virtual surgery).

The display unit 30 outputs the graphic display of the simulation session. As detailed hereinafter, the display unit 30 may be a monitor with 2D or 3D display, a tablet, etc. The display unit 30 may be also be a VR headset, among possibilities. The display unit 30 in its various forms may also provide an augmented reality (AR) output, for instance in the case of telesurgery.

A haptic system 40 is another master device manipulated by the user of the system 10 to control corresponding slave devices in the simulation session, or in a telesurgery session, in preparation for or in conclusion to impaction with the impactor mechanism 20.

The virtual surgery processor unit 50 executes the VR surgery simulation session in the exemplary embodiment, or in a telesurgery session.

A robotic slave system 60 may also be part of the system 10, in the context of a telesurgery use of the impactor mechanism 20.

Figure 5:
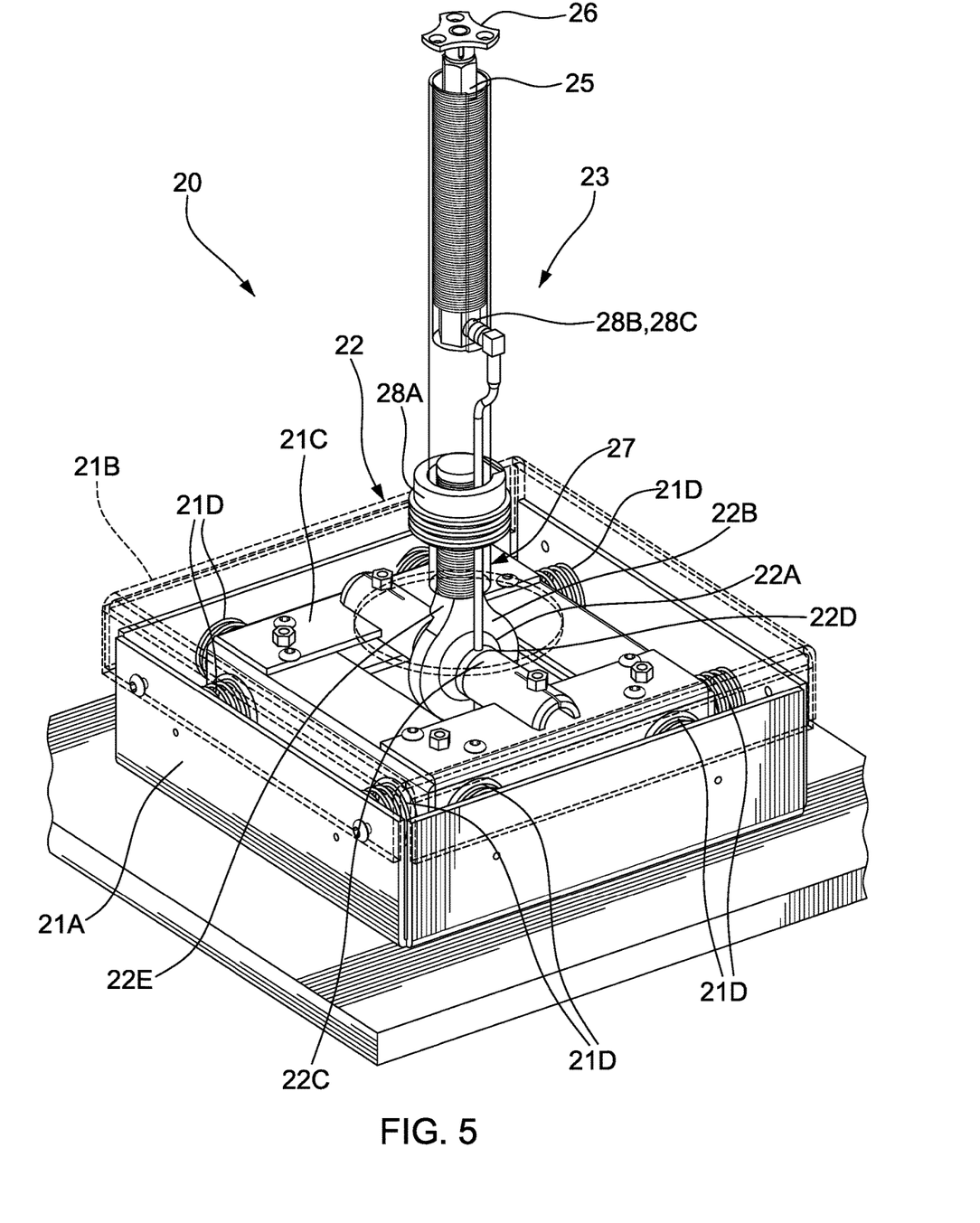
FIG. 5 is a perspective view of an embodiment of the impactor mechanism of FIG. 1.
Figure 6:
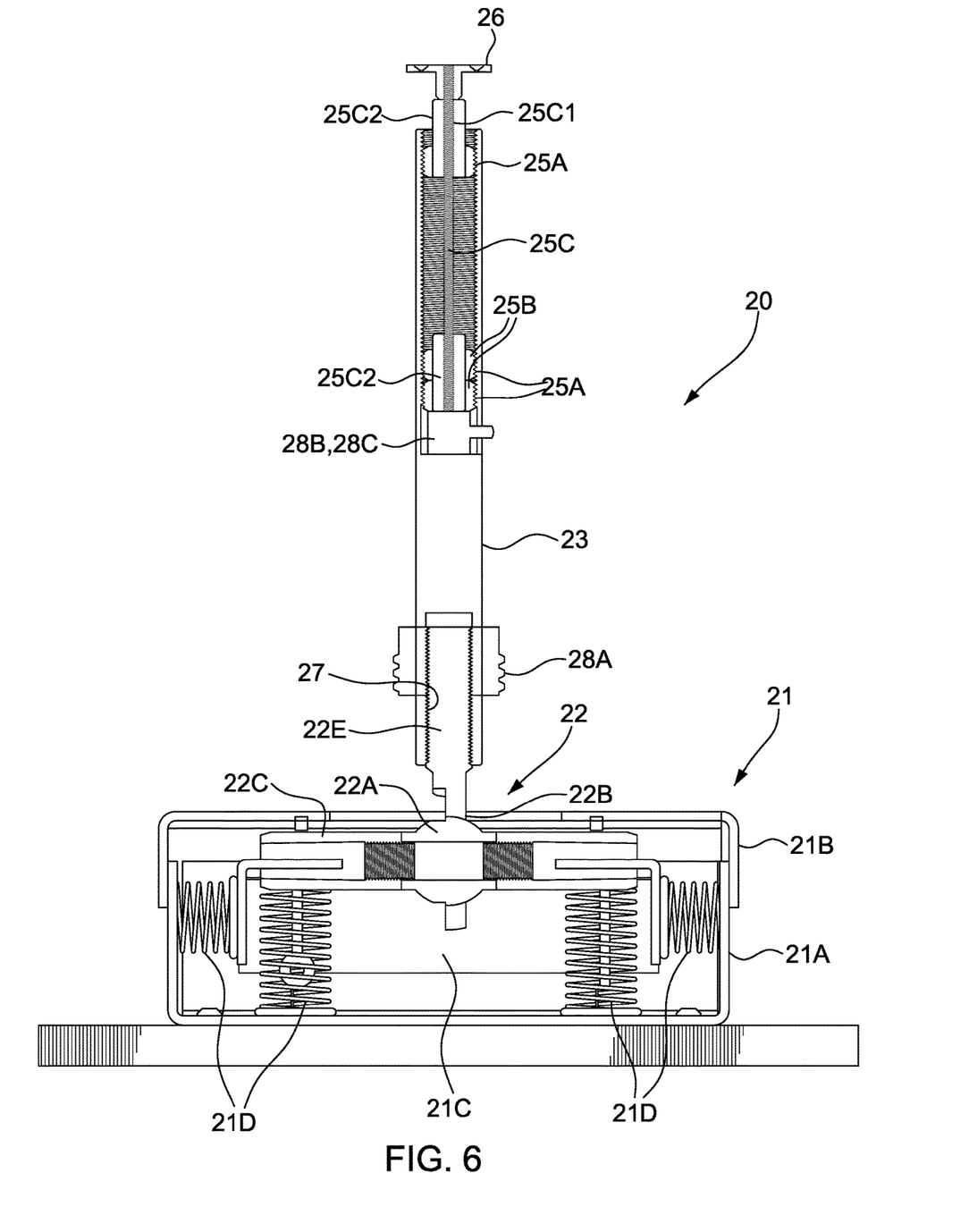
FIG. 6 is a sectional view of the impactor mechanism of FIG. 5.

Referring to FIG. 1, the impactor mechanism 20 may have a base 21. The base 21 may be a standalone base or may be integrated to a support table. As the base 21 may receive impacts with a lateral vector(s) during impacting, it is preferably made of a sturdy material to withstand impact forces. The base 21 may also be anchored to a support table or platform to stand still while receiving the impacts. The base 21 may also be referred to as a housing, casing, block, etc. Referring to FIG. 5, an exemplary embodiment of the impactor mechanism 20 is shown, with the base 21 including a casing 21A with cover 21B. The casing 21A is of the type that may be anchored to a structure, such as a support table of the system 10. The cover 21B may be releasably connected to a remainder of the casing 21A, for providing an access to an inner cavity of the casing 21A. Other embodiment include access from a bottom (e.g., an inverted open box, etc). The cover 21B may have an opening, such as a central opening, for an impactor shaft to project out of the casing 21A. The base 21 in the embodiment of FIGS. 5 and 6 may also have a block 21C, that may include various mechanical parts of the impactor mechanism 20, as detailed hereinafter. Because of some play, the block 21C may move relative to the casing 21A. In an embodiment, the block 21C may move in two or more translational degrees of freedom, such as in a planar movement relative to a plane of a support table. The block 21C may be floating, and held in place by shock absorbing components. Shock absorbing components may be provided between the casing 21A and the block 21C, for instance in opposition to movement in the two horizontal translations. In an embodiment, there are shock absorbing components between the block 21A and a bottom plane supporting the block 21C, whether this support plane is part of the casing 21A or of support table or structure, as shown in FIG. 6. As illustrated, the shock absorbing components may be coil springs 21D, though other components may be used, such as dampers, rubber pads, cylinders, dashpots, etc. In another embodiment, the mechanical parts are connected directly to walls of the casing 21A. In another embodiment, the block 21C is connected directly to the support table or structure, without casing 21A, for instance as interfaced by vertical coil springs 21D or like shock absorbing components. As yet another embodiment, the shock absorption components could be in a shaft or joint of the impactor mechanism 10.

The base 21 houses a rotational joint 22 providing at least two rotational degrees of freedom (DOF), such as a ball forming a ball joint with the base 21, or like rotational joint. Appropriate sensors are integrated into the base 21 in order to track movements of the ball 22 as a result of manipulations of a master impactor. The sensors may be optical sensors, rotary encoders, LEDs with imaging array of photodiodes, inertial sensors, among numerous possibilities, to track two or three DOFs of the ball 22 relative to the base 21. Referring to FIG. 5, an embodiment of the rotational joint features a rod end bearing 22 (a.k.a., heim joint, rose joint) including a ball swivel 22A in a circular casing 22B. The rod end bearing 22 may also have or may interact with a rod 22C secured or rotatably mounted to the block 21C. In an embodiment, as shown in FIG. 5, the rod 22C is part of the block 21C. A bearing 22D may be in the ball swivel 22A to rotatably interface the ball swivel 22A to the rod 22C. The bearing 22D may be a low friction sleeve (e.g., PTFE, ceramic), a rolling element bearing (e.g., roller bearing). Therefore, two or more rotational DOFs are enabled by the bearing 22, i.e., about two or more intersecting axes, namely one being aligned with the rod 22C, one transverse to the axis of the rod 22C, and another aligned with the shaft 23. In an embodiment, when the impactor mechanism 20 is on a support table, the axis aligned with the rod 22C and the axis transverse to the rod 22C are horizontal. Still referring to FIG. 5, the rod end bearing 22 may also include a shaft portion 22E. As shown, the shaft portion 22E may be a threaded shaft portion that is connected to the impactor shaft 23. In another embodiment, the shaft portion 22E is the impactor shaft.

Other joints that may be used include a universal joint, or interconnected rotational joints. The use of a ball joint is well suited for impaction, considering that the position of the center of rotation of the ball 22 is fixed in the base 21. In an embodiment, the base 21 may have an hemispherical interface surface in contact with the ball 22 on a substantial portion of the spherical surface of the ball 22, whereby the connection is robust and suited to withstand impacts. Some rotational constraints may be applied to the rotational joint to mimic rotational resistance of an acetabular cup relative to the acetabulum in the virtual session or in the telesurgery session. In terms of other joints, the joint 22 may include translational joints providing one or two DOFs of translation, for example in a plane more or less parallel to that of the table. This may for example be achieved by the constrained movement enabled by the shock absorbing components, such as the coil springs 21D, rubber blocks, etc. The resulting movement(s) may emulate the movement of a tool removing osteoma or osteophytes by impaction (e.g., such as a chisel).

The master impactor may have different configurations, including one with an impactor shaft 23 and an impactor handle 24, as in FIG. 1. The impactor shaft 23 is shown as being straight, with a first end connected to the ball 22, and a second end operationally connected to the handle 24. The shaft 23 may be connected in any appropriate way to the ball 22, including an integral monoblock fabrication, a screwing engagement, etc. In the embodiment of FIG. 5, the impactor shaft 23 is threadingly engaged to the threaded shaft portion 22E of the rod end bearing 22. The shaft 23 is also shown as being substantially straight, but other shapes are considered as well. For example, the shaft 23 may have an offset to emulate an offset impactor. By having a releasable connection between the ball 22 and the shaft 23, such as the screwing engagement (for example, as in FIG. 5), the shafts may be interchanged to enable different shapes and sizes of shaft 23 to be used, to enable the use of different master impactor shapes and sizes in training or telesurgery sessions.

The handle 24 may or may not be present, as a user may simply hold the shaft 23. In an embodiment, the handle 24 is sized to be representative of existing handle sizes and grips, to procure a real feel to the master impactor. According to an embodiment, the handle 24 is mounted to the shaft 23 by way of a translation joint 25 used to simulate the translation occurring during impaction, as the acetabular cup is forced into the acetabulum. The translation joint 25 may be actuated as a function of the impact force and calculated or measured resistance from the acetabular cup entering the acetabulum, in the virtual session or in the telesurgery session, respectively. For example, the translation joint 25 between the shaft 23 and the handle 24 may be a linear actuator or pneumatic/hydraulic cylinder actuated proportionally to calculated or measured resistance and impact force to provide force feedback to the user. Other shock absorption means may be provided on the master impactor. The translation joint 25 may also include a passive shock absorber, such as a spring, pneumatic, and/or hydraulic damper, or combinations thereof. In yet another embodiment, there is no translation joint 25, and consequently, no force feedback on the impaction. According to an embodiment, with reference to FIGS. 5 and 6, the shaft 23 is tubular, and has an end of the translation joint 25 projecting out of the impact end of the shaft 23. Accordingly, it is the end of the translation joint 25 that receives the impacts. In the exemplary embodiment of FIGS. 5 and 6, the translation joint 25 has hollow-lock set screws 25A threadingly engaged in the inner cavity of the shaft 23, the inner cavity having corresponding threading. The hollow-lock set screws 25A may also be known as supports, sliders, jam set screws, or simply set screws, etc. The hollow-lock set screws 25A, three being shown (but one or more being potentially present), each have a central bore 25B. The central bore 25B may have any appropriate shape (circular, square, etc), but in an embodiment the central bore 25B is non circular. For example, the central bore 25B is hexagonal. This may facilitate the engagement of the hollow-lock set screws 25A in the shaft 23, for example by the use of an Allen key. The central bore(s) 25B may also be concentrically positioned in the shaft 23. The translation joint 25 may further include rod 25C. The rod 25C may have different configurations, including the one illustrated of a threaded rod portion 25C1 with sleeves 25C2 thereon. The sleeves 25C2 have a shape complementary to that of the central bores 25B, such as hexagonal. Therefore, as seen in the arrangement of FIG. 6, the sleeves 25C2 are in sliding engagement in the central bores 25B. If the central bores 25B are non-circular, the movement of the rod 25C will be substantially translational (i.e., one degree of freedom of translation). As an alternative to the non-circularity, other mechanisms may be used to constrain the movements to a translation. Moreover, while a combination of a threaded rod portion 25C1 and sleeves 25C2, other arrangements are considered for the rod 25C, such as a monoblock body. The rod 25C may also be received directly in the shaft 23, in sliding engagement, i.e., without the hollow-lock set screws 25A.

A head 26 may be located at the end of the handle 24, and thus act as impactor head. In the embodiment of FIGS. 5 and 6, the head 26 is screwingly engaged to the threaded rod portion 25C1, though it may also be a monoblock part of the rod 25C in an alternative embodiment. The head 26 may include any appropriate sensors to measure the forces applied to the master impactor during impaction. The sensors in the head 26 may include a force sensor measuring the axial force resulting from the hammering on the master impactor. The force sensor may be supplemented by torque sensors to measure bending of the master impactor, as bending may be symptomatic of lateral forces/side loads during impaction. For example, the bending loads are measured about two axes, transverse to the longitudinal axis of the master cylinder. Although described as being in the sensor head 26, the force and torque sensors may be located at any appropriate locations on the master impactor, such as at any point along the axis of the shaft 23 or handle 24, or in the spherical joint. In an embodiment, the force and torque sensors are located in a portion of the shaft 23 adjacent to the ball 22. This lower portion of the shaft 23 may be separable from a remainder of the shaft 23 and handle 24, as shown at joint 27 (for instance the joint 27 is the threaded engagement between the threaded shaft portion 22E of the rod end bearing 22 and the shaft 23). Such an arrangement is practical if various sizes, shapes and configurations of master impactor are to be used in training or telesurgery, as the sensors may remain connected to the system 10 while impactor configurations are interchanged. Additional degrees of freedom of force and torque may be measured although this may not be necessary, notably in simulation or telesurgery acetabular cup impaction.

The orientation of the master impactor is measured by way of the sensors in the spherical joint, as described previously, for example in two rotational degrees of freedom. It may not be necessary to determine an orientation of the master impactor about its longitudinal axis as such a rotation does not affect the orientation of the acetabular cup. The various sensors of the impactor mechanism 20 are shown as orientation sensors 28A, force sensor(s) 28B and torque sensor(s) 28C in FIGS. 3 and 4. The orientation sensors 28A are those determining the orientation of the master impactor, for its real-time tracking. The orientation sensors 28A may be any type of sensor, such as inertial sensors (accelerometers, gyroscope, inclinometers), optical encoders, etc. The force sensor(s) 28B are used to measure the impact force. The force sensors 28B may be strain gauges, etc. The torque sensor(s) 28C measure bending of the master impactor. The torque sensors 28C may be strain gauges, etc. The force sensors 28B and/or the torque sensors 28C may include one or more strain gauge load cells, piezoelectric load cells, hydraulic load cells, pneumatic load cells, vibrating string load cells, capacitive load cells, among other possibilities. A hammer or like impacting tool is shown at 29 in FIG. 1. Referring to FIGS. 5 and 6, the force sensor 28B is shown inside the shaft 23, in communication with the translation joint 25, to quantify the impacts received on the sensor head 26. Since the force on the rod 25C is transmitted directly to the force sensor 28B, without absorption or damping through springs or other means, the measured force is representative in magnitude to forces that would be transmitted to an impactor. Moreover, since the shock absorption components (e.g., coil springs 21D) are located below the force sensors 28B/28C, the force transmitted to the base 21 and support table is spread over time, which decreases the amplitude of its peak value, but extends its effect in time. It also have a reflective effect, returning some of the transmitted energy to the user's hand holding the shaft, for feedback. This may have a protective effect on surrounding equipment. Still in the embodiment of FIG. 5, the orientation sensors 28A are for example accelerometers surrounding the shaft 23, at or near the junction with the rod end bearing 22. The orientation sensors 28A may be located elsewhere along the shaft 23, for instance closer to the joint end than to the impact end.

Still referring to FIGS. 1 and 2, the system 10 has a display unit 30, shown as being a vertical monitor. The system 10 may have more than one display unit 30, including a horizontal monitor 30A in FIG. 2, to enable a user of the system 10 to overlook an anatomical location 31 displayed by the system 10 during a virtual surgery session, and hence reproduce the point of view of an operator in surgery. A secondary vertical monitor 30B may be provided for other personnel to view actions resulting from the interaction between the main user and the system 10 via the primary monitor 30A. Referring to FIG. 1, the anatomical location 31 is shown in the context of hip arthroplasty, or acetabular cup implanting. The anatomical location 31 includes an acetabular cup 32, an impactor 33, and retractors 34. The display may be a graphic user interface and/or computer generated graphics including simulation models, in the case of VR simulation, or may be live camera footage in telesurgery, in which the anatomical location 31 and instruments 32, 33 and 34 are real. It bears mentioning that other instruments and bones may be displayed in hip surgery, including cup reamers, drills, etc, and those may be displayed as well, prior to or after impaction. The display of the display unit 30 also has a frame of reference shown as X, Y, Z in FIG. 1. The frame of reference may also be known as coordinate system, a referential system, etc. The orientation of the master impactor of the impactor mechanism 20 is calibrated to match the orientation of the impactor 33 in the frame of reference on the display unit 30, at least during impaction steps. Likewise, any generic tool supported by the haptic system 40 is tracked during virtual sessions in the frame of reference of the display, for the concurrent movement of slave instruments in the virtual session. Other information may be displayed on the monitor 30B, such as pre-operative or intraoperative medical images (e.g., X-rays, scans, MRI models, etc), navigational data. In an embodiment, the monitor 30B may be a tablet like monitor enabling touch interfaces by the user of the system 10.

The haptic system 40 is shown as having any appropriate force-feedback manipulator 41 supporting one or more mock-up surgical tools 42. For example, the mock-up surgical tools may be interchanged during a procedure as a function of a surgical flow. The force-feedback manipulator 41 is shown as having a parallel configuration, although a serial arm could be used as well. The haptic system 40 includes a tracking apparatus 43, to determine the position and orientation of the surgical tools 42, and hence control the slave tools 33 and 34 as a function of the tracking in the frame of reference of the system 10. The tracking apparatus 43 may employ any appropriate technology, such as joint sensors (rotary encoders, optical sensors, etc), inertial sensors, optical tracking, etc. The tracking apparatus is globally shown as 43, but it is to be understood that the tracking apparatus 43 may include numerous components in the force-feedback manipulator 41. Likewise, some of the actuators of the force-feedback manipulator 41 may be located in the casing labelled tracking apparatus 43. The force-feedback manipulator 41 has haptic capacity, for instance by actuators and a transmission (e.g., gears, tendons, etc) for a user to receive force feedback as a function of forces occurring at the slave side of the system 10.

As observed in the figures, the impactor mechanism 20 is shown being separated from the haptic system 40. By decoupling the impacting instrumentation from the mock-up instrumentation, the system 10 provides robust hardware for the higher force, lower accuracy maneuvers, and precise instrument for the higher DOF, lower force maneuvers. Therefore, the haptic system 40 is not hampered by a force-feedback manipulator 41 (a.k.a., haptic system feedback 41) capable of withstanding impacting forces at any orientation. As an alternative embodiment, the impactor mechanism 20 may be releasably coupled to the haptic system 40 during impaction simulation or impaction use. In such an arrangement, the force-feedback manipulator 41 may provide force feedback against rotation of the shaft 23 relative to the base 21, while the base 21 absorbs the impacting forces. In a further non-limitative embodiment, the various orientation sensors (e.g., 28A) may be removed from the impactor mechanism 20 when the impactor mechanism 20 is connected to the force-feedback manipulator 41, with the tracking system 43 tracking the orientation of the shaft 23. In another embodiment, the impactor mechanism 20 is operated without force feedback.

Figure 3:
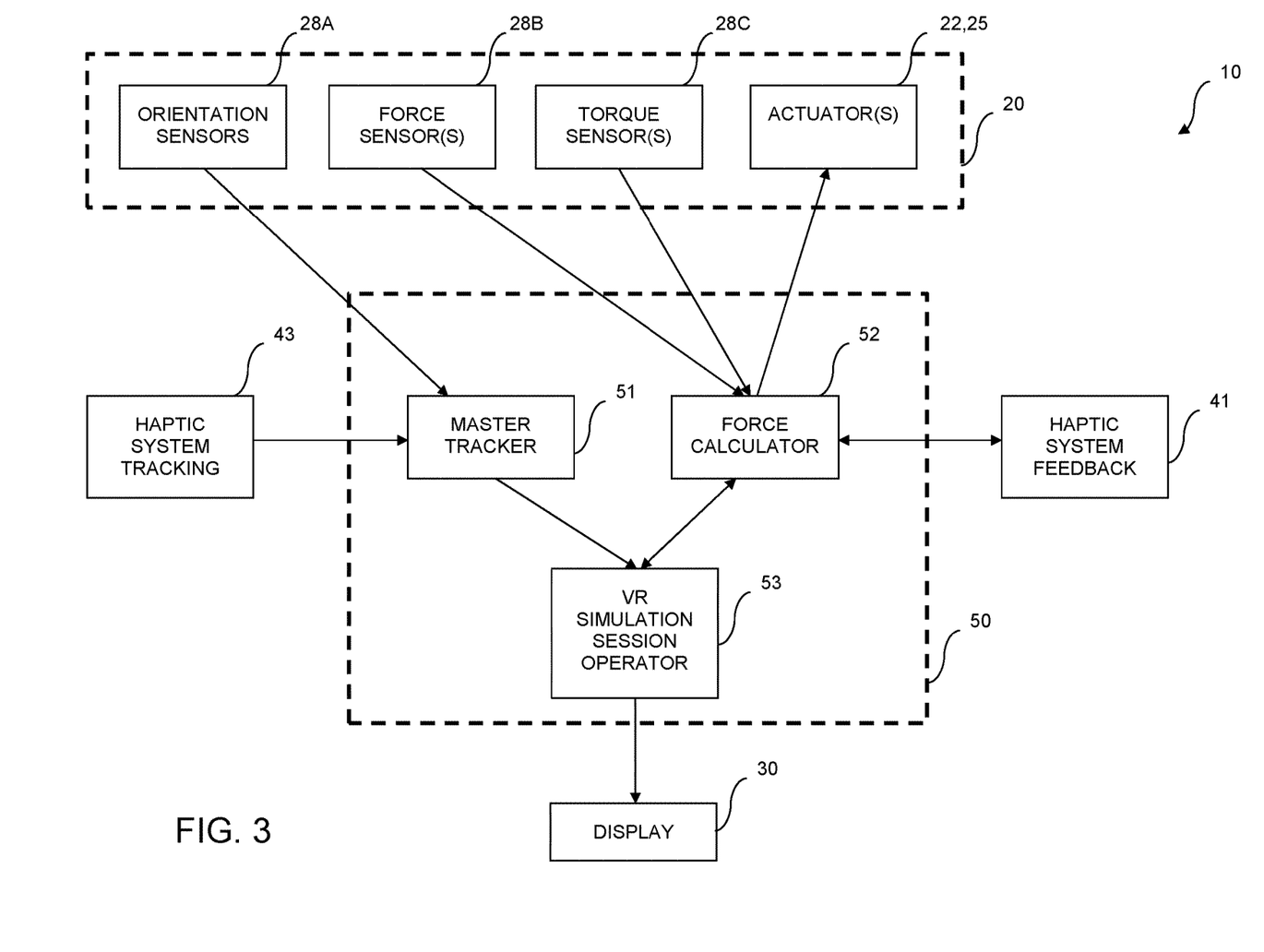
FIG. 3 is a block diagram of a virtual surgery processor unit for operating the impactor mechanism of FIG. 1, in virtual reality surgery simulation.

Referring to FIG. 3, the virtual surgery processor unit 50 executing the VR surgery simulation session is shown in greater details. The virtual surgery processor unit 50 is any processor (laptop, computer, etc) having suitable processing speed in order to perform VR surgery simulation or telepresence surgery (a.k.a., telesurgery) in real-time, i.e., to produce real-time graphic rendering of manipulations of master devices in virtual sessions. The virtual surgery processor unit 50 may also optionally produce real-time force feedback to master devices during the virtual sessions. The virtual surgery system processor unit 50 may therefore have various modules that perform steps and functions as described hereinafter. The various steps and modules may be in the form of computer program products with a computer-readable memory storing computer executable instructions thereon that, when executed by a computer such as the virtual surgery processor unit 50, perform the method steps and/or functions described herein.

The virtual surgery processor unit 50 may have a master tracker module 51, tasked with tracking an orientation of the master impactor (e.g., impactor 20) via signals provided by the orientation sensors 28A. If the haptic system 40 is part of the system 10, the master tracker module 51 may receive signals from the tracking apparatus 43 (FIG. 2) as well, to track the position and/or orientation of mock-up instrumentation. The master tracker module 51 may be configured to filter out readings of the orientation sensors 28A having occurred during impaction: such impacts may have an effect on the readings of given types of orientation sensors 28A, such as accelerometers. By filtering out such values, the orientation readings may be more stable over time. One contemplated method to filter out is to correlate the impact forces with the orientation readings on a time scale, and remove orientation readings at instants of measured impacts.

The virtual surgery processor unit 50 may have a force calculator module 52 that measures the forces (e.g., including torque) during impaction on the impactor mechanism 20. The measuring is done using the signals received from the force sensor(s) 28B and the torque sensor(s) 28C. The force calculator module 52 may optionally drive the actuators present at the joints 22 and 25 if these joints are actuatable, based on calculated force feedback from the slave end of a virtual session. The force calculator module 52 may optionally drive the actuators present in the force-feedback manipulator 41 if the latter is used in conjunction with the impactor mechanism 20 as described above, again based on calculated force feedback from the slave end of a virtual session. If the haptic system 40 is part of the system 10, the force calculator module 52 may receive signals from the force-feedback manipulator 42 (FIG. 2), to measure force inputs on the mock-up instrumentation and drive the force-feedback manipulator 42 in providing force feedback to a user as a function of forces originating from actions in or at the slave end of the virtual session. The force calculator module 52 may also amplify, filter, over-sample, threshold, the raw data from the force sensors 28B, to ensure the proper assessment of the forces. Such functions may be performed at the force sensors 28B as well.

A VR simulation session operator 53 runs the virtual simulation session. Among other functions, the VR simulation session operator 53 controls the session flow, i.e., the sequences of steps of the session in accordance with a simulated surgical procedure. The VR simulation session operator 53 may also receive tracking data from the master tracker module 51 and force data from the force calculator module 52 and consequently determine the position and orientation of corresponding slave objects in the VR simulation, in the frame of reference. The VR simulation session operator 53 may therefore determine interactions, such as contacts, alterations, between virtual slave objects at the virtual slave end of the simulation, in response to the tracking by the master tracker module 51. Consequently, the VR simulation session operator 53 may output force feedback data for the force calculator module 52 to drive the actuator(s) 22 and 25 if present, though the force feedback may be optional. Moreover, the VR simulation session operator 53 may generate graphics depicting a virtual slave end, as shown at 31 in FIG. 1, for display on the display unit 30. The graphics are updated in real-time by the virtual surgery processor unit 50 as a function of manipulations of the master instrumentation.

In the particular context of impaction, the VR simulation session operator 53 may include a cup orientation calculator module. The cup orientation calculator module may calculate current cup implant orientation from a tracking of the orientation of the master impactor by the master tracker module 51. The cup orientation calculator module may express the current cup implant orientation in the VR simulation, i.e., the orientation of the slave impactor relative to the pelvis in angles in the frontal, sagittal, and/or transverse planes. The cup orientation calculator module may also or alternatively express the current cup implant orientation as abduction and inclination values. This may help the user of the system 10 to properly orient the master impactor of the impactor mechanism 20.

Once a desired cup implant orientation is reached, the impacting may be performed by the user. The VR simulation session operator 53 may include an impacting assessor module to assess if the right force and right angle are input on the impactor mechanism 20 to achieve the desired cup implant orientation. The impacting assessor module receives tracking data from the master tracking module 51, the force data from the force calculator module 52, as well as interactions between virtual objects, such as between virtual cup 32 and virtual acetabulum. The interactions may be in the form of virtual models with virtual frictional forces and size data, according to which data the resistance to penetration of the virtual cup 32 in the virtual acetabulum may be determined. With this data, the impacting assessor module determines any variation of orientation of the cup from the desired cup implant orientation, as a result of non-axial impacting/hand movement on the impactor mechanism 20. The impacting assessor module may also provide corrective values or qualitative information to explain any form of variation in the impacting. The corrective values may be in a real-time update of inclination and abduction values, for example, as well as a variation value, such as a percentage, relative to the desired cup implant orientation. The qualitative information may be in the form of observations: holding-hand shift during impacting, impact with non-negligible side load (e.g., right, left, up, down), excessive force, or excess impacts. All information is consequently displayed on the display unit 30. Moreover, the system 10 may have the capacity of emitting sounds indicative of actions and warnings, for example. The sound emission may be part of the feedback provided to the user.

Figure 4:
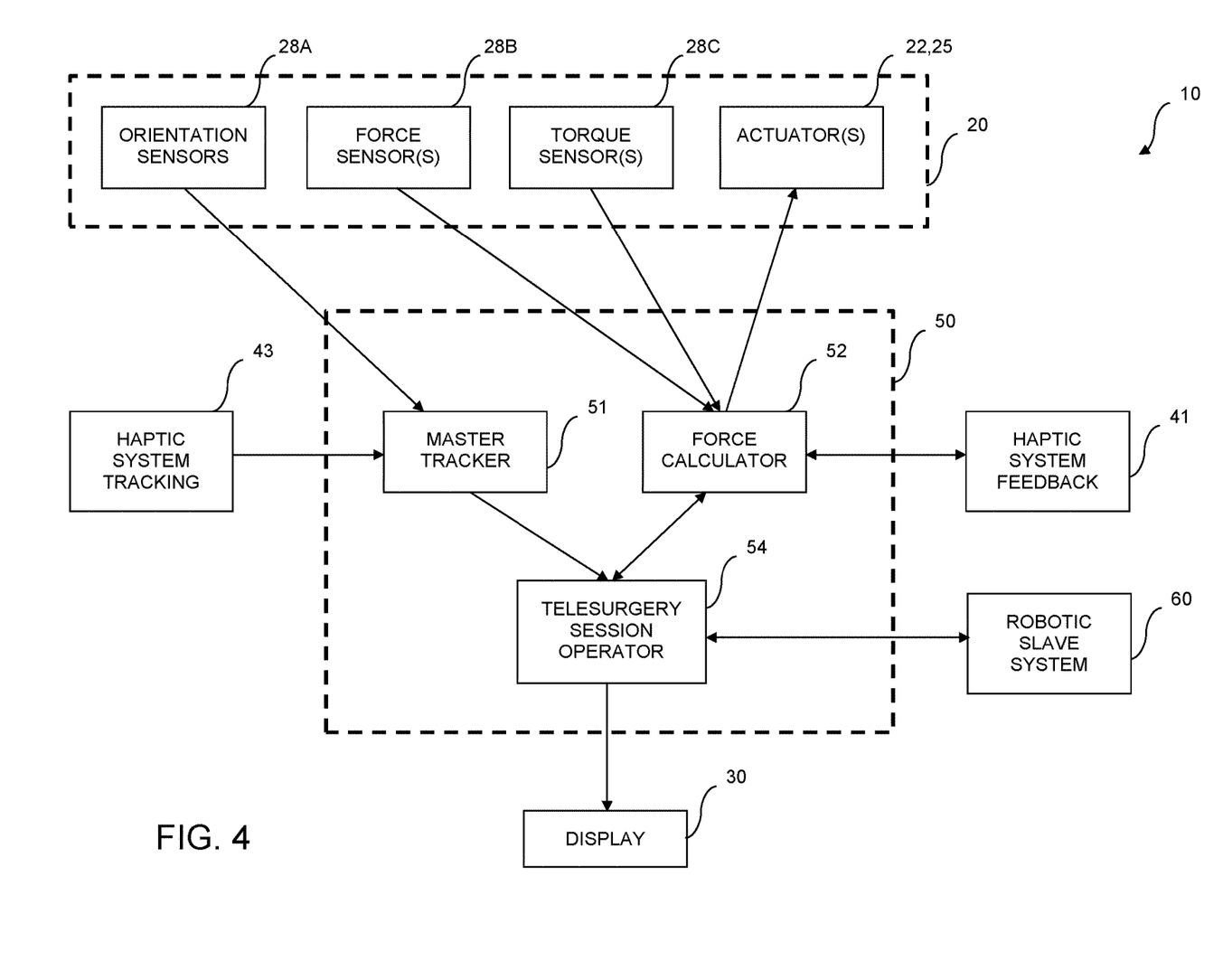
FIG. 4 is a block diagram of a virtual surgery processor unit for operating the impactor mechanism of FIG. 1, in telesurgery.

The detailed description provided for FIG. 3 refers to the VR surgery simulation. However, as shown in FIG. 4, the impactor mechanism 20 may also be employed in remote virtual surgery for instance with a robotic slave system 60 performing real surgery remotely. The robotic slave system 60 may consequently include a processor unit similar to the one shown at 50. The system 10 is similar whether it runs a VR surgery simulation as in FIG. 3, or a telesurgery procedure as in FIG. 4, whereby like numerals will refer to like components.

In FIG. 4, the virtual surgery processor unit 50 has a telesurgery session operator 54 running the telesurgery surgery session. Among other functions, the telesurgery session operator 54 controls the session flow, i.e., the sequences of steps of the session in accordance with a surgical procedure, and as a response of bilateral communication with the robotic slave system 60. The telesurgery session operator 54 may also receive tracking data from the master tracker module 51 and force data from the force calculator module 52 and consequently drive or send information to the robotic slave system 60. The telesurgery session operator 54 may receive force feedback and positional data for the slave objects at the robotic slave system 60. Consequently, the telesurgery session operator 54 may output force feedback data for the force calculator module 52 to drive the actuator(s) 22 and 25 if present, or the force-feedback manipulator 41 if used, though the force feedback is optional with the impactor mechanism 20. Moreover, the telesurgery session operator 54 may treat video footage taken by the robotic slave system 60, with additional navigational data added, such as virtual axes and values, for display on the display unit 30 (e.g., augmented reality). The navigational data may be updated in real-time by the virtual surgery processor unit 50 as a function of manipulations of the master instrumentation.

In the particular context of impaction, the telesurgery session operator 54 may also include the cup orientation calculator module, operating in a similar fashion as for the VR simulation session operator 53 (FIG. 3). The cup orientation calculator module may calculate current cup implant orientation from a tracking of the orientation of the master impactor by the master tracker module 51. The cup orientation calculator module may express the current cup implant orientation, i.e., the orientation of the slave impactor relative to the pelvis in angles in the frontal, sagittal, and/or transverse planes at the robotic slave system 60. The cup orientation calculator module may also or alternatively express the current cup implant orientation as abduction and inclination values. This may help the user of the system 10 to properly orient the master impactor of the impactor mechanism 20.

Once a desired cup implant orientation is reached, the impacting may be performed by the user, and cause impaction at the robotic slave system 60, although the robotic slave system 60 may impact the cup at the slave end based on the desired cup implant orientation. In the event that impaction is transmitted from master to slave, the telesurgery session operator 54 may include an impacting assessor module to assess if the right force and right angle are input on the impactor mechanism 20 to achieve the desired cup implant orientation. The impacting assessor module receives tracking data from the master tracking module 51, the force data from the force calculator module 52, as well as interactions between bone and instruments at the slave end. With this data, the impacting assessor module determines any variation of orientation of the cup from the desired cup implant orientation, as a result of non-axial impacting/hand movement on the impactor mechanism 20. The impacting assessor module may also provide corrective values to explain any form of variation in the impacting. The corrective values may be in a real-time update of inclination and abduction values, for example, as well as a variation value, such as a percentage, relative to the desired cup implant orientation. All information is consequently displayed on the display unit 30.

The present disclosure has been focusing on acetabular cup placement, it is contemplated to use the impactor mechanism 20 for other procedures in which impacting is required. As a few non-exhaustive example, the system 10 with the impactor mechanism 20 may be used to simulate or perform in telesurgery the removal of osteoma and osteophytes with chisel-like tools, the impaction of an intramedullary nail or rod in a medullary canal of a long bone, the positioning of a cut or drill guide in knee arthroplasty, bone graft impaction, intervertebral implant insertion, impaction of femoral knee prosthesis, shoulder prosthesis, elbow prosthesis. The impactor mechanism 20 is self-standing, self-support, and/or independent from a haptic system. By having the base 21 at the impact end, a substantial portion of the impacts transmitted to the base 21 are spread to a structure of the system 10, as opposed to being transmitted to a mechanism such as a haptic or robotic arm.

The invention claimed is:

1. An impactor mechanism for virtual or telepresence surgery comprising:
a base;
an impactor shaft having a first end and a second end, a handle portion being provided at the second end;
at least one rotational joint between the first end of the impactor shaft and the base, the joint providing at least two rotational degrees of freedom to the impactor shaft; and
sensors in the impactor mechanism for measuring an orientation of the impactor shaft relative to the base, and for measuring at least an impact force on the impactor shaft, for use in virtual or telepresence surgery.

2. The impactor mechanism according to claim 1, wherein the at least one rotational joint is a spherical joint.

3. The impactor mechanism according to claim 2, wherein the spherical joint is a rod end bearing, with a rod of the rod end bearing connected to the base.

4. The impactor mechanism according to claim 3, wherein the rod of the rod end bearing is fixed to the base.

5. The impactor mechanism according to claim 3, wherein the rod is generally horizontal.

6. The impactor mechanism according to claim 3, wherein the rod end bearing has a threaded shaft portion, the impactor shaft being threadingly engaged to the threaded shaft portion.

7. The impactor mechanism according to claim 1, further comprising a releasable connection between the impactor shaft and the at least one rotational joint.

8. The impactor mechanism according to claim 1, wherein the base has a block connected to the at least one joint, a casing receiving the block, and at least one translational joint between the block and the casing providing at least one translational degree of freedom.

9. The impactor mechanism according to claim 8, comprising two of the translational joint, the block displaceable in a horizontal plane.

10. The impactor mechanism according to claim 8, comprising at least one shock absorption device opposing a force against movement in each said translation degree of freedom.

11. The impactor mechanism according to claim 10, wherein the at least one shock absorption device is at least one coil spring.

12. The impactor mechanism according to claim 1, further comprising a translational joint at the second end of the impactor shaft, the translational joint being connected to an impactor head at the second end.

13. The impactor mechanism according to claim 12, wherein the shaft has a tubular portion, the translational joint being received in a cavity of the tubular portion.

14. The impactor mechanism according to claim 13, wherein one of the sensors is at least one force sensor in the cavity.

15. The impactor mechanism according to claim 12, wherein a direction of the translational joint is parallel to a longitudinal axis of the impactor shaft.

16. The impactor mechanism according to claim 12, wherein the translational joint includes at least one hollow-lock set screw received in the cavity of the tubular portion, the translational joint having a rod slidingly engaged in the at least one hollow-lock set screw.

17. The impactor mechanism according to claim 16, wherein the rod has at least one sleeve interfaced with the at least one hollow-lock set screw, the sleeve being on a threaded rod portion of the rod.

18. The impactor mechanism according to claim 1, wherein axes of the at least two rotational degrees of freedom intersect each other.

19. The impactor mechanism according to claim 1, wherein the sensors include at least one accelerometer on the impactor shaft.

20. The impactor mechanism according to claim 1, wherein the sensors include at least one torque sensor.

* * * * *